United States Patent
Tisdell et al.

(10) Patent No.: US 8,759,356 B2
(45) Date of Patent: Jun. 24, 2014

(54) COMPOUNDS AND METHODS FOR CONTROLLING FUNGI

(75) Inventors: Francis E. Tisdell, Carmel, IN (US); James M. Renga, Indianapolis, IN (US); William C. Lo, Fishers, IN (US); Maurice C. H. Yap, Zionsvile, IN (US); David H. Young, Carmel, IN (US); George E. Davis, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 513 days.

(21) Appl. No.: 12/772,248

(22) Filed: May 3, 2010

(65) Prior Publication Data
US 2010/0298143 A1 Nov. 25, 2010

Related U.S. Application Data

(60) Provisional application No. 61/179,402, filed on May 19, 2009.

(51) Int. Cl.
*A01N 43/54* (2006.01)
*C07D 239/42* (2006.01)
*C07D 401/04* (2006.01)
*A61K 31/505* (2006.01)
*C07D 239/30* (2006.01)

(52) U.S. Cl.
CPC ............ *A61K 31/505* (2013.01); *C07D 239/30* (2013.01)
USPC .......................................... 514/256; 544/326

(58) Field of Classification Search
CPC ............................ C07D 239/30; A61K 31/505
USPC ............ 544/211, 330, 326; 546/304; 514/256
See application file for complete search history.

(56) References Cited

U.S. PATENT DOCUMENTS

| | | | | |
|---|---|---|---|---|
| 4,791,110 A * | 12/1988 | Arnold et al. | ................ | 514/247 |
| 5,250,530 A * | 10/1993 | Giencke et al. | ............... | 514/256 |
| 6,686,469 B2 * | 2/2004 | Eberle et al. | ................ | 544/319 |
| 6,780,869 B1 * | 8/2004 | Green et al. | .................. | 514/275 |
| 6,825,199 B2 * | 11/2004 | Domagala et al. | ....... | 514/252.16 |
| 2007/0259919 A1 * | 11/2007 | Rheinheimer et al. | ........ | 514/334 |
| 2009/0042917 A1 * | 2/2009 | Bessho et al. | ................. | 514/273 |
| 2011/0086759 A1 * | 4/2011 | Aspinall et al. | ............... | 504/103 |

FOREIGN PATENT DOCUMENTS

| | | |
|---|---|---|
| DE | 10 2007 061756 | 6/2009 |
| EP | 0 031 257 | 7/1981 |
| GB | 1345640 A * | 1/1974 |
| WO | WO 9744326 A1 * | 11/1997 |
| WO | WO-00/66565 | 11/2000 |
| WO | WO 03026661 A1 * | 4/2003 |
| WO | WO-2004/035588 | 4/2004 |
| WO | WO-01/38311 | 5/2005 |
| WO | WO 2007083692 A1 * | 7/2007 |
| WO | WO 2007084560 A2 * | 7/2007 |
| WO | WO-2008/107096 | 9/2008 |
| WO | WO-2009/076440 | 6/2009 |
| WO | WO 2009080242 A1 * | 7/2009 |
| WO | WO-2009/125870 | 10/2009 |

OTHER PUBLICATIONS

L.Loru et al, Annales de la Société Entomologiquo de France, 46(3-4), 422-424 (2010).*
S. Robev, Doklady Bolgarskoi Akademii Nauk, 34(12), 1677-80 (1981).*
L. Del Corona et al., 26 European Journal of Medicinal Chemistry, 729-733 (1991).*
Y. Nishimura et al., 30 Journal of Medicinal Chemistry, 1622-1626 (1987).*

(Continued)

*Primary Examiner* — Deepak Rao
*Assistant Examiner* — Alexander R Pagano
(74) *Attorney, Agent, or Firm* — C. W. Arnett; Faegre Baker Daniels LLP

(57) ABSTRACT

Various aspects disclosed herein relate to aryl substituted aminopyrimidines according to Formula 1:

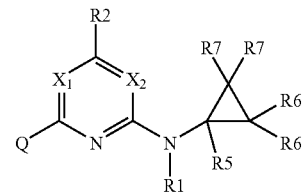

wherein, $X_1$ is N or C—$R_3$; $X_2$ is N or C—$R_4$ provided that $X_1$ and $X_2$ are not both N; $R_1$-$R_7$ are H, CN, CHO, —SCN, $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C-7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocycle, wherein the substituents are one or more of the following F, Cl, Br, OH, CN, $NO_2$, CHO, —SCN, $S(O)n$-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino; C1-C4-alkyl-S(O)=NH; and Q is a substituted or unsubstituted aryl, substituted or unsubstituted heterocycle wherein the substituents of Q are taken from $R_1$-$R_7$.

4 Claims, No Drawings

(56) References Cited

OTHER PUBLICATIONS

International Searching Authority, International Search Report for PCT/US2010/33327, issued Apr. 8, 2010.

Stevens K L et al: Synthesis and Evaluation of Pyrazolo[1,5-b]pyridazines as Selective Cyclin Dependent Kinase Inhibitors Bioorganic & Medicinal Chemistry Letters, Pergamon, Nov. 2008, vol. 18, No. 21, pp. 5758-5762, Elsevier Science, GB.

Kim D K et al: Synthesis and Biological Evaluation of Trisubstituted Imidazole Derivatives as Inhibitors of p38alphamitogen-activated Protein Kinase, Bioorganic & Medicinal Chemistry Letters, Pergamon, Jul. 2008, vol. 18, No. 14, pp. 4006-4010, Elsevier Science, GB.

Fricker M et al: Substituting c-Jun N-terminal kinase-3 (JNK3) ATP-binding Site Amino Acid Residues with their p38 Counterparts Affects Binding of JNK-and p38-selective Inhibitors, Archives of Biochemistry and Biophysics, Jun. 2005, vol. 438, No. 2, pp. 195-205, Academic Press, US.

\* cited by examiner

COMPOUNDS AND METHODS FOR CONTROLLING FUNGI

CROSS-REFERENCE TO RELATED APPLICATIONS

This Application claims the benefit of U.S. Provisional Application 61/179,402 filed on May 19, 2009, which is expressly incorporated by reference herein.

FIELD OF THE INVENTION

This invention relates to the synthesis of aryl substituted aminopyrimidines and methods of using theses compounds to control various fungi including some plant pathogens.

BACKGROUND

Fungi comprise one of the largest and perhaps most diverse kingdoms of eukaryotic life. Taxonomists have already characterized some 70,000 different species and estimate that the entire kingdom may encompass some one and a half million different species. A number of these organisms are a source of food such as mushrooms and some are the source of useful chemicals such as some antibiotics. The primary role of most fungi in the ecosystem is to recycle organic matter and many fungi are involved in the process of decaying plant matter. Unfortunately, a large number of fungi are known to grow at the expense of useful materials and perhaps more importantly commercially important plants that are essential to human survival.

Given their diversity and impact on industries such as agriculture, compounds and methods for controlling fungi receive a lot of attention. Currently, a number of fungicides have been identified and synthesized and are currently used to protect both ornamental plants and food crops from pathogenic fungi. And while many safe and effective fungicides are currently in use, the evolution of pathogenic fungi and the ever increasing pressures to use lower levels of fungicides in part to reduce costs continues to create the need for new fungicides and/or effective means of using existing fungicides. It is one object of this instant disclosure to address this on-going need.

SUMMARY

One embodiment is an aryl substituted aminopyrimidine according to Formula 1:

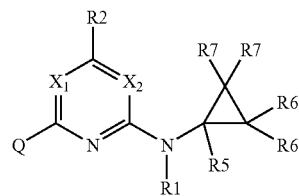

wherein, $X_1$ is N or C—$R_3$; $X_2$ is N or C—$R_4$ provided that $X_1$ and $X_2$ are not both N; $R_1$-$R_7$ are H, CN, CHO, —SCN, $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C-7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocycle, wherein the substituents are one or more of the following F, Cl, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino; C1-C4-alkyl-S(O)=NH; and Q is a substituted or unsubstituted aryl, substituted or unsubstituted heterocycle wherein the substituents of Q are taken from $R_1$-$R_7$.

Another embodiment is an a fungicidal composition, comprising at least one compound according to Formula 1 and a phytologically acceptable carrier.

In still another embodiment the antifungal formulation further includes at least one additional compound selected from the group consisting of: insecticides, and herbicides.

Another embodiment is a method for controlling a fungal infestation, comprising the steps of providing at least one compound according to claim 1; and applying the compound to a surface adjacent to a fungal infestation.

Still another embodiment is a compound selected from the group of aryl substituted aminopyrimidines consisting of:

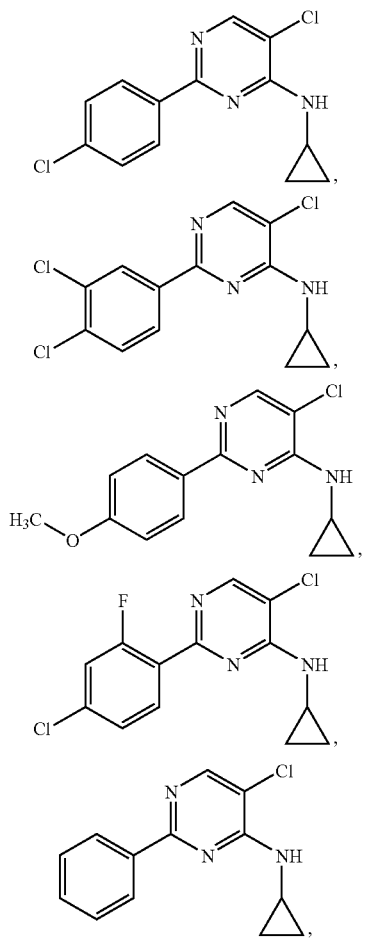

-continued

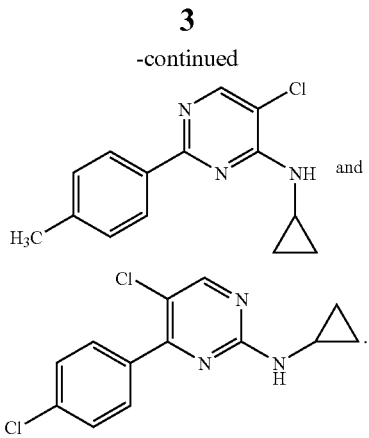

and

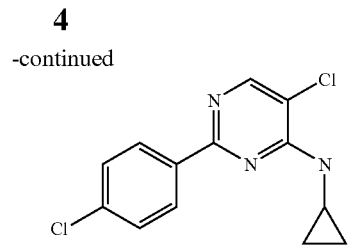

Still another embodiment is an anti-fungicidal composition, comprising at least one compound according to the above aryl substituted aminopyrimidines and a phytologically acceptable carrier.

In still another embodiment, the composition includes at least one additional compound selected from the group consisting of: insecticides, fungicides, and herbicides.

Another embodiment is a method of controlling a fungal infestation, comprising the steps of: providing at least one compound according to the group of aryl substituted aminopyrimidines illustrated herein; and applying the compound to a surface adjacent to a fungal infestation.

Another embodiment is a method of controlling fungal infestation, comprising the steps of: providing at least one compound according to Formula 1; and applying the compound to a surface adjacent to a fungal infestation.

DESCRIPTION

For the purposes of promoting an understanding of the principles of the novel technology, reference will now be made to the various exemplary embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Example 1

Scheme 1, a synthesis of compound 1:

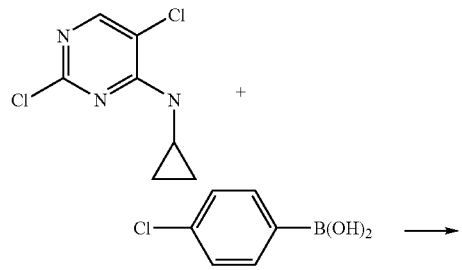

Briefly, 2,5-dichloro-4-cyclopropylaminopyrimidine (1 mmol., 204 mg) was dissolved in dimethoxyethane (8 ml) and 4-chlorophenyl boronic acid (1.5 mmol, 234 mg), sodium carbonate (2 mmol., 2 ml of a 1 molar aqueous solution), and tetrakis (triphenylphosphine) palladium (0.05 mmol, 60 mg) was added. The reaction was heated to reflux for 4 hours and stirred overnight at 25° C. Next the reaction mixture was filtered through silica gel using ethyl acetate; then concentrated and chromatographed using 15% ethyl acetate in hexane to afford the product as a white solid. wgt. 138 mg. 49% yield MP 103-105° C. GC/MS 279; $H^1$ NMR (CDCl3) ppm 8.36 (d, 2H, J=0.03 Hz); 8.26 (s, 1H); 7.42 (d, 2H, J-0.03 Hz); 5.55 (sb, 1H); 2.98 (m, 1H); 0.98 (m, 1H); 0.68 (m, 1H).

Method of Testing the Fungicidal Activity of Various Compounds Disclosed Herein.

The compounds of the present invention have been found to have significant fungicidal effect, particularly for agricultural use. Many of the compounds are particularly effective for use with agricultural crops and horticultural plants. In particular, the compounds have the potential to effectively control a variety of undesirable fungi that infect useful plant crops as illustrated by the examples herein. Activity has been demonstrated for fungi, including for example the following representative fungi species: brown rust of wheat (*Puccinia recondita tritici*—PUCCRT); *septoria* blotch of wheat (*Septoria tritici*—SEPTTR).

Referring now to Table 1, some of the exemplary compounds were tested in order to measure their ability to either prevent or cure fungal infections. A given compound's preventative properties were determined by treating a susceptible test plant with the exemplary compound and then exposing the plant to fungal spores. A given compound's curative properties were determined by first exposing a susceptible plant to an infective fungus and then applying the exemplary fungicidal compounds.

It will be understood by those in the art that the efficacy of the compounds against the foregoing fungi establishes the general utility of the compounds as fungicides. The activity of the compounds as effective fungicides was determined by applying the compounds to plants and observing control of fungal disease. The compounds were formulated at rates of 50 ppm and 200 ppm in 10 vol. % acetone plus 90 vol. % Triton X water (deionized water 99.99 wt %+0.01 wt % Triton X100), giving a "formulated test compound." Formulated test compounds were applied to plants using a turntable sprayer fitted with two opposing air atomization nozzles which delivered approximately 1500 L/ha of spray volume.

Again referring to Table 1, tests were carried out to determine a given exemplary compound's ability to prevent or at least limit a fungal infection as follows. All plants in the study were inoculated with spores of the fungus in this case either PUCCRT or SEPTTR) the day after treatment with the putative fungicide. Next, the plants were incubated in an environment conducive to disease development. Disease severity was evaluated 7 to 25 days later, depending on the speed of disease development. The following experiments were performed in the laboratory to determine the fungicidal efficacy of the compounds of the invention.

Measuring the Protective Effect of Various Compounds Against Leaf Rust of Wheat (Causal Agent Bayer Code PUCCRT).

Wheat plants (variety 'Yuma') were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit the spores to germinate and to infect the leaf. The plants were then transferred to a greenhouse until disease developed on untreated control plants. These tests were carried out using two different levels of the compound, 50 ppm and 200 ppm, see Table 1.

Measuring the Preventative Effect of Various Compounds Against *Septoria* Blotch of Wheat (Causal Agent Bayer Code SEPTTR).

Wheat plants (variety 'Yuma') were grown from seed in a 50% pasteurized soil/50% soil-less mix until the seedlings had a fully expanded first leaf. Each pot contained 3-10 seedlings. These plants were sprayed until wet with the formulated test compound. On the following day, the leaves were inoculated with an aqueous spore suspension of *Septoria tritici* and the plants were kept in high humidity (one day in a dark dew chamber followed by three days in a lighted dew chamber) to permit the spores to germinate and to infect the leaf. The plants were then transferred to a greenhouse until disease developed on untreated control plants. These tests were carried out using two different levels of the compound, 50 ppm and 200 ppm, see Table 1.

Measuring the Curative Effect of Various Compounds Against *Septoria* Blotch of Wheat (Causal Agent Bayer Code SEPTTR).

Wheat plants (variety 'Yuma') were grown from seed in a mixture of about 50% pasteurized soil/50% soil-less mix until the seedlings had a fully expanded first leaf. Each pot contained 3-10 seedlings. These plants were inoculated with an aqueous spore suspension of *Septoria tritici* and the plants were kept in high humidity (one day in a dark dew chamber followed by two days in a lighted dew chamber) to permit the spores to germinate and to infect the leaf. The plants were then removed form the dew chamber and allowed to dry. After drying, the inoculated plants were sprayed until wet with the formulated test compound. On the following day, the plants were transferred to a greenhouse until disease developed on untreated control plants. These tests were carried out using two different levels of the compound, 50 ppm and 200 ppm, see Table 1.

Disease control was determined by visually estimating the percent disease severity in treated and untreated pots 7 to 24 days after inoculation, depending on speed of disease development. Evaluations were typically made 7 or 8 days after inoculation for PUCCRT and 18 to 22 days after inoculation for SEPTTR. Percent disease control (% DC) was calculated by: % DC=(1−% Disease severity treated/% disease severity untreated)*100.

The compounds of this invention may be preferably applied in the form of a composition comprising one or more of the compounds of Formula 1 with a phytologically-acceptable carrier. The compositions include, for example, concentrated formulations which are dispersed in water or another liquid for application, or are dust or granular formulations which are applied without further treatment. The compositions may be prepared according to procedures which are conventional in the agricultural chemical art, but which are novel and important because of the presence therein of the compounds disclosed herein.

TABLE 1

Representative aryl substituted aminopyrmidines and their curative and protective activity measured at 50 and 200 ppm-against the pathological fungi *Septoria tritici* (SEPTTR) and *Puccinia recondita* (PUCCRT)

| Molecular Structure | Reference Number | Percent Disease Control | | | | | |
|---|---|---|---|---|---|---|---|
| | | One Day Protectant | | | | Three Day Curative | |
| | [ppm]: | 50 | 200 | 50 | 200 | 50 | 200 |
| | | SEPTTR | | PUCCRT | | SEPTTR | |
| 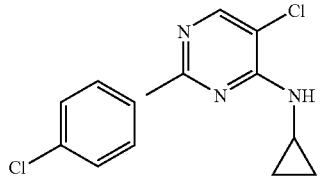 | 1 | 90 | 97 | 93 | 97 | 0 | 0 |
| 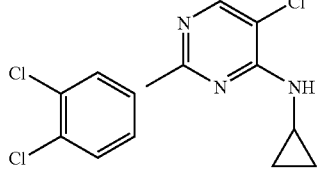 | 2 | 0 | 35 | 0 | 0 | 62 | 72 |

TABLE 1-continued

Representative aryl substituted aminopyrmidines and their curative and protective activity measured at 50 and 200 ppm-against the pathological fungi *Septoria tritici* (SEPTTR) and *Puccinia recondita* (PUCCRT)

| | | Percent Disease Control | | | | | |
|---|---|---|---|---|---|---|---|
| | | One Day Protectant | | | | Three Day Curative | |
| Molecular Structure | [ppm]: Reference Number | 50 | 200 | 50 | 200 | 50 | 200 |
| | | SEPTTR | | PUCCRT | | SEPTTR | |
| 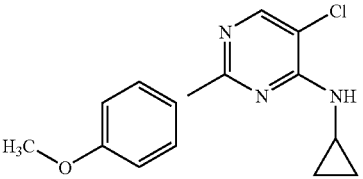 | 3 | 74 | 85 | 99 | 97 | 0 | 0 |
| 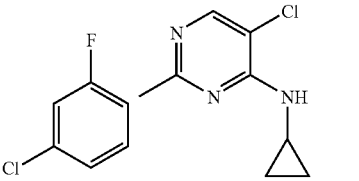 | 4 | 38 | 86 | 50 | 99 | 0 | 18 |
| 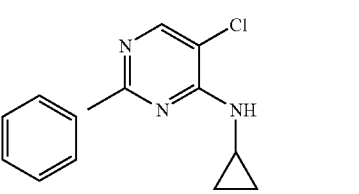 | 5 | 38 | 90 | 99 | 99 | 0 | 0 |
| 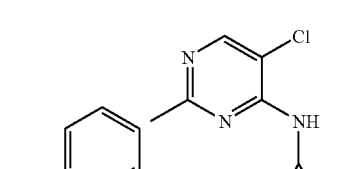 | 6 | 65 | 95 | 97 | 99 | 0 | 27 |
| 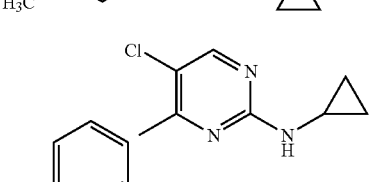 | 7 | 91 | 61 | 53 | 0 | 50 | 50 |

The dispersions in which the compounds are applied are most often aqueous suspensions or emulsions prepared from concentrated formulations of the compounds. Such water-soluble, water suspendable, or emulsifiable formulations are either solids, usually known as wettable powers, or liquids, usually known as emulsifiable concentrates, or aqueous suspensions. The present invention contemplates all vehicles by which the compounds of this invention can be formulated for delivery for use as a fungicide. As will be readily appreciated, any material to which these compounds can be added may be used, provided they yield the desired utility without significantly interfering with the fungicidal activity of the compounds of this invention.

Wettable powders, which may be compacted to form water dispersible granules, comprise an intimate mixture of the active compound, an inert carrier, and surfactants. The concentration of the active compound is usually from about 10 percent weight/weight (% w/w) to about 90% % w/w, and more preferably about 25% to about 75% w/w. In the preparation of wettable powder compositions, the active ingredients can be compounded with any of the finely divided solids, such as prophyllite, talc, chalk, gypsum, Fuller's earth, bentonite, attapulgite, starch, casein, gluten, montmorillonite clays, diatomaceous earths, purified silicantes or the like. In such operations, the finely divided carrier is ground or mixed with the toxicant in a volatile organic solvent. Effective surfactants, comprising from about 0.5% to about 10% of the wettable powder, that can be used in combination with the inventive compounds, include sulfonated lignins, naphthalenesulfonates, alkylbenzenesulfonates, alyl sulfates, and non-ionic surfactants such as ethylene oxide adducts of alkyl phenols.

Emulsifiable concentrates of the compounds of this invention comprise a convenient concentration, such as from about 10% to about 50% w/w, in a suitable liquid. Briefly, one method for creating these emulsions includes the step of dissolving the compound in an inert carrier (either a water miscible solvent or a mixture of water-immiscible organic solvents and emulsifiers). The concentrates may be diluted with water and oil to form spray mixtures in the form of oil-in-water emulsions. Useful organic solvents that can be used to practice the invention, include aromatics, especially the high-boiling naphthalenic and olefini portions of petroleum such as heavy aromatic naphtha and the like. Other organic solvents may also be used such as, for example, terpenic solvents including rosin derivatives, aliphatic ketones, such as cyclohexanone, and complex alcohols such as 1-ethoxyethanol.

Emulsifiers which can be advantageously employed herein can be readily determined by those skilled in the art and include various non-ionic, anionic, cationic, and amphoteric emulsifiers, or a blend of two or more emulsifiers. Examples of non-ionic emulsifiers useful in preparing the emulsifiable concentrates include, for example, the polyalkylene glycol ethers and condensation products of alkyl and aryl phenols, aliphatic alcohols, aliphatic amines, or fatty acids with ethylene oxide, propylene oxides such as the ethoxylated alkyl phenols, and carboxylic esters solubilised with polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulphated polyglycol ethers, and appropriate salts of phosphated polyglycol ether.

Representative organic liquids which can be employed in preparing the emulsifiable concentrates of the present invention include aromatic liquids such as zylene, propyl benzene fractions or mixed naphtlalene fractions, mineral oils, substituted aromatic organic liquids such as dioctyl phthalate, kerosene, and dialkyl amides of various fatty acids; particularly the dimethyl amides of fatty glycols and glycol derivatives such as the n-butyl ether, ethyl ether, or methyl ether of triethylene blycol. Mixtures of two or more organic liquids are also often suitably employed in the preparation of the emulsifiable concentrate. The preferred organic liquids are xylene and propyl enzene fractions, with xylene being most preferred. The surface active dispersing agents are usually employed in liquid compositions and in the amount of from about 0.1 weight % (wt. %) to about 20 (wt. %) of the combined weight of the dispersing agent and active compound. The active compositions can also contain other compatible additives, for example, plant growth regulators and other biologically active compounds used in agriculture.

Aqueous suspensions may comprise suspensions of water-insoluble compounds of this invention, dispersed in an aqueous vehicle at a concentration in the range of from about 5% to about 50% w/w. In one embodiment, suspensions are prepared by finely grinding the compound and vigorously mixing it into a vehicle comprised of water and surfactants chosen from the type of surfactants as discussed above. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions which are particularly useful when applying the composition to the soil. Granular compositions may include from about 0.5% w/w of to about 10% w/w of the compound dispersed in an inert carrier comprising entirely or in large part of a coarsely divided attapulgite, bentonite, diatomite, clay, or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing, and drying to obtain the desired granular particle.

Dusts including the compounds may be prepared by intimately mixing the compound in powdered form with a suitable dusty agricultural carrier such as, for example, kaolin clay, ground volcanic rock, and the like. Many such dusts can suitably include from about 1% w/w to about 10% w/w of the compound.

The active compositions may contain adjuvant surfactants to enhance properties such as deposition, wetting, and penetration of the compositions onto the target crop and organism. These adjuvant surfactants may optionally be employed as a component of the formulation or as part of a tank mix. The amount of adjuvant surfactant may vary from about 0.01 percent volume/volume of (% v/v)percent to 1.0% v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines, and blends of surfactants with mineral or vegetable oils.

The compositions may optionally include combinations which comprise at least 1% of one or more of the compounds of this invention with another agriculturally active ingredient (AI). Such additional AI may include for example fungicides, insecticides, nematocides, miticides, arthropodicides, bactericides, herbicidal, or combinations thereof that are compatible with the compounds of the present invention in the medium selected for application, and not antagonistic to the activity of the present compounds. Accordingly, in such embodiments, the other AI is employed as a supplemental AI for the same or for a different use with plants than the inventive compounds. The compounds in combination can generally be present in a ratio of from about 1:10 to about 100:1.

The present invention includes within its scope methods for the control or prevention of fungal attack. These methods comprise applying the active compounds to the locus of the fungus, or to a locus in which the infestation is to be prevented (for example applying it to a cereal or grape plant. The compounds are suitable for treatment of various plants at fungicidal levels while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds, or foliage of plants for the control of various fungi without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect, particularly for agricultural use. Many of the compounds are particularly effective for use with agricultural crops and horticultural plants, or with wood, paint, leather, or carpet backing.

In particular, the compounds effectively control a variety of undesirable fungi which infect useful plant crops. In addition to the fungi tested, these compounds will likely have activity against a variety of fungi, including, for example, the following representative fungi species: downy mildew of grape (*Plasmopara viticola*—PLASVI), late blight of tomato (*Phytophthora infestants*—PHYTIN), apple scab (*Venturia inaequalis*—VENTIN), brown rust of wheat (*Puccinia recondite*—PUCCRT), stripe rust of wheat (*Puccinia striiformis*—PUCCST), rice blast (*Pyricularia oryzae*—PYRIOR), *Cercospora* leaf spot of beet (*Cercospora beticola*—CERCBE), powdery mildew of wheat (*Erysiphe graminis*—ERYSGT), leaf blotch of wheat (*Septoria tritici*—SEPTTR), sheath blight of rice (*Rhizoctonia solani*—RHIZSO), eyespot of wheat (*Pseudocercosporella herpotrichoides*—PSDCHE), brown rot of peach (*Monilinia fructicola*—MONIFC), and glume blotch of wheat (*Leptosphaeria nodorum*—LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired. The fungal species to be controlled and the stage of growth thereof, as well as the part of the plant or other product to be contacted with the toxic active ingredient. Thus, all the active ingredients of the compounds of this invention, and compositions containing the same, may not be equally effective at similar concentrations or against the same fungal species. The compounds of this invention and compositions are effective in use with plants in a disease inhibiting and phytologically acceptable amounts.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A compound, selected from the group consisting of:

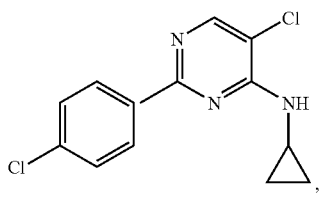

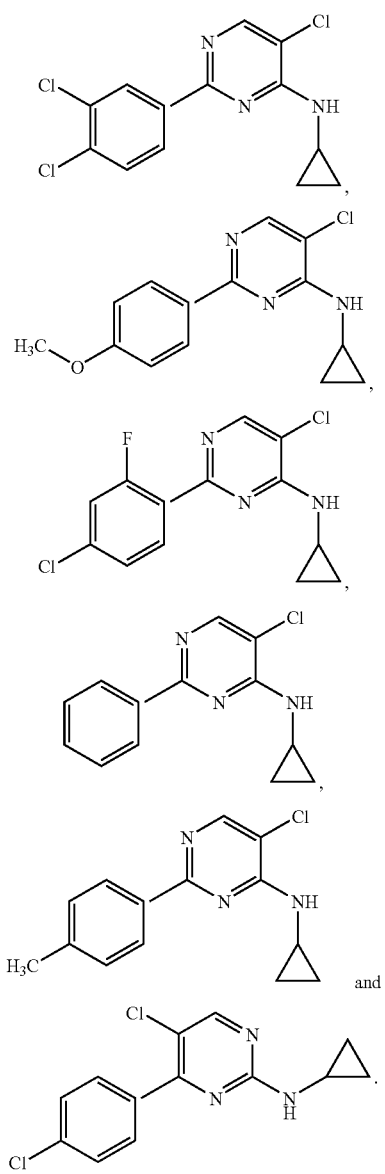

2. A fungicidal composition, comprising at least one compound according to claim 1, and a phytologically acceptable carrier.

3. The composition according to claim 2, further including at least one additional compound selected from the group consisting of: insecticides, fungicides, and herbicides.

4. A method of controlling a fungal infestation, comprising the steps of:
   providing at least one compound according to claim 1; and
   applying the compound to a surface adjacent to a fungal infestation.

* * * * *